(12) United States Patent
Ihn (10) Patent No.: US 9,417,213 B1
(45) Date of Patent: Aug. 16, 2016

(54) NON-DESTRUCTIVE EVALUATION SYSTEM FOR AIRCRAFT

(75) Inventor: Jeong-Beom Ihn, Bellevue, WA (US)

(73) Assignee: THE BOEING COMPANY, Chicago, IL (US)

( * ) Notice: Subject to any disclaimer, the term of this patent is extended or adjusted under 35 U.S.C. 154(b) by 1272 days.

(21) Appl. No.: 13/179,695

(22) Filed: Jul. 11, 2011

(51) Int. Cl.
*G01N 29/00* (2006.01)
*G01N 29/22* (2006.01)
*G01N 29/44* (2006.01)

(52) U.S. Cl.
CPC ............... *G01N 29/22* (2013.01); *G01N 29/44* (2013.01)

(58) Field of Classification Search
CPC .............. G01N 29/043; G01N 29/07; G01N 2291/0427; G01N 2291/048; G01N 29/22; G01N 29/44
USPC .......................................................... 73/632
See application file for complete search history.

(56) References Cited

U.S. PATENT DOCUMENTS

| | | | | |
|---|---|---|---|---|
| 4,523,468 A * | 6/1985 | Derkacs | ............... | G01N 29/07 73/598 |
| 4,937,453 A * | 6/1990 | Nelson | ............... | G01T 1/2018 250/370.09 |
| 5,176,142 A * | 1/1993 | Mason | ............... | A61B 8/12 600/463 |
| 5,181,514 A * | 1/1993 | Solomon | ............... | A61B 8/12 600/152 |
| 5,189,915 A * | 3/1993 | Reinhart | ............... | G01N 29/043 73/623 |
| 5,191,791 A * | 3/1993 | Gerardi | ............... | B64D 15/16 73/178 R |
| 5,313,834 A * | 5/1994 | Lagace | ............... | B06B 1/06 73/187 |
| 5,320,104 A * | 6/1994 | Fearnside | ............... | A61B 8/12 600/447 |
| 5,431,054 A * | 7/1995 | Reeves | ............... | G01N 29/043 73/612 |
| 5,461,653 A * | 10/1995 | Parker | ............... | G21K 1/025 378/155 |
| 5,563,346 A * | 10/1996 | Bartelt | ............... | G01S 15/8925 600/447 |
| 5,911,158 A * | 6/1999 | Henderson | ............... | G01L 1/16 310/328 |
| 6,087,652 A * | 7/2000 | O'Meara | ............... | G01D 5/26 250/208.1 |
| 6,691,578 B1 * | 2/2004 | Puskas | ............... | B08B 3/12 134/113 |
| 6,834,113 B1 * | 12/2004 | Liljehag | ............... | H04R 5/02 181/144 |
| 6,996,480 B2 * | 2/2006 | Giurgiutiu | ............... | G01M 5/0033 702/159 |
| 7,024,315 B2 * | 4/2006 | Giurgiutiu | ............... | G01N 29/11 702/33 |
| 7,032,454 B2 * | 4/2006 | Amano | ............... | G06K 9/0002 73/702 |
| 7,212,605 B2 * | 5/2007 | Danielsson | ............... | G01T 1/1644 378/146 |
| 7,333,898 B2 * | 2/2008 | Griess | ............... | H04Q 9/00 702/35 |
| 7,596,470 B2 | 9/2009 | Kim | | |
| 7,647,206 B2 * | 1/2010 | Ford | ............... | G01N 29/4409 702/183 |
| 7,743,659 B2 * | 6/2010 | Kearns | ............... | G01M 5/00 73/632 |
| 7,881,881 B2 * | 2/2011 | Giurgiutiu | ............... | G01N 29/2475 702/39 |
| 7,917,311 B2 * | 3/2011 | Finkel | ............... | G01B 17/04 702/39 |

(Continued)

*Primary Examiner* — Harshad R Patel
*Assistant Examiner* — Samir M Shah
(74) *Attorney, Agent, or Firm* — Yee & Associates, P.C.

(57) ABSTRACT

A method and apparatus comprises a transducer and an array of transducers. The transducer is associated with an object. The transducer has an elongate shape. The array of transducers is associated with the object. The array of transducers is substantially parallel to the transducer.

17 Claims, 5 Drawing Sheets

(56) References Cited

U.S. PATENT DOCUMENTS

| | | | | |
|---|---|---|---|---|
| 8,269,400 B2* | 9/2012 | Sato | ......................... | A61B 8/06 310/334 |
| 8,286,490 B2* | 10/2012 | Ruzzene | ................. | G01S 15/88 73/596 |
| 8,344,725 B2* | 1/2013 | Fischer | ................. | G01N 27/82 324/220 |
| 8,513,860 B2* | 8/2013 | Paget | .................... | H04R 17/00 310/328 |
| 8,544,328 B2* | 10/2013 | Sohn | .................... | G01N 29/043 73/598 |
| 2006/0095223 A1* | 5/2006 | Gordon | ................. | G01N 29/07 702/116 |
| 2007/0261495 A1* | 11/2007 | Van Der Ent | ...... | G01N 29/2456 73/622 |
| 2008/0212805 A1* | 9/2008 | Fincham | ................ | H03G 3/004 381/160 |
| 2009/0016552 A1* | 1/2009 | Medley | .................. | H04R 19/02 381/191 |
| 2009/0055106 A1* | 2/2009 | Finkel | .................... | G01B 17/04 702/39 |
| 2010/0206080 A1* | 8/2010 | Ruzzene | ................. | G01S 15/88 73/618 |
| 2010/0251821 A1* | 10/2010 | Mizota | ................ | G01N 29/262 73/602 |
| 2010/0264778 A1* | 10/2010 | Paget | .................... | H04R 17/00 310/322 |
| 2010/0274161 A1 | 10/2010 | Azhari et al. | | |
| 2011/0277549 A1* | 11/2011 | Frederick | ............... | G01N 29/07 73/627 |

\* cited by examiner

NON-DESTRUCTIVE EVALUATION SYSTEM FOR AIRCRAFT

GOVERNMENT LICENSE RIGHTS

This application was made with United States Government support under contract number F33615-03-2-3300 awarded by the United States Air Force. The United States Government has certain rights in this application.

BACKGROUND INFORMATION

1. Field

The present disclosure relates generally to aircraft structures and, in particular, to detecting inconsistencies in aircraft structures. Still more particularly, the present disclosure relates to a method and apparatus for non-destructive evaluation of aircraft structures to detect inconsistencies.

2. Background

Aircraft structures may be inspected at different times to determine whether the aircraft structures have desired properties. For example, an aircraft structure may be inspected during and after manufacturing of the structure. The aircraft structure also may be inspected prior to using the aircraft structure within an aircraft or after the aircraft structure has been integrated into the aircraft.

For example, skin panels for an aircraft may be inspected during manufacturing of the skin panels. An inspection may be performed to determine whether undesired inconsistencies are present in the skin panels prior to installation of the skin panels in the aircraft.

After installation of the skin panels on the aircraft, an inspection may be performed to determine whether an undesired inconsistency is present in the skin panels on the aircraft. An inconsistency may occur as a result of stresses and/or loads placed on the skin panels during flight, takeoff, landing, and/or other phases of flight. Exposure to the environment also may cause an inconsistency to form in the skin panels. In some cases, the inconsistency may be an undesired inconsistency that requires maintenance. If an undesired inconsistency is detected in a skin panel, the skin panel may be reworked or replaced on the aircraft.

The inspections may be performed using non-destructive evaluation (NDE) tests. A non-destructive evaluation test is a test in which an evaluation of a structure is made without causing an undesired change to the structure. Examples of non-destructive evaluation testing techniques include, for example, ultrasonic inspection, magnetic particle inspection, remote visual inspection, eddy current sensor inspection, and/or other suitable types of testing techniques that do not alter a structure in an undesired manner.

Currently, inspections of an aircraft for inconsistencies are performed based on a schedule. This schedule may depend on the age of the aircraft, the number of flights made by the aircraft, results of prior inspections, and/or other suitable factors.

The inspection may include testing particular locations on the aircraft. Some locations may include structures that may be known to have inconsistencies form in the structures over time.

Some of the different non-destructive evaluation tests may require disassembling one or more aircraft structures to reach the particular location for an inspection. For example, a skin panel may be removed to reach a rib, spar, or other structure. Oftentimes, the locations of interest for the inspection may be hidden or more difficult to access than desired.

When the inspection is done, the aircraft structures are then reassembled. Sometimes the disassembly and reassembly of these aircraft structures may cause inconsistencies to form in the aircraft structures. Additionally, this type of inspection may result in the aircraft being out of service for more time than desired.

Therefore, it would be advantageous to have a method and apparatus that takes into account at least some of the issues discussed above, as well as possibly other issues.

SUMMARY

In one advantageous embodiment, an apparatus comprises a transducer and an array of transducers. The transducer is associated with an object. The transducer has an elongate shape. The array of transducers is associated with the object. The array of transducers is substantially parallel to the transducer.

In another advantageous embodiment, a nondestructive evaluation system for an aircraft comprises a first unit and a second unit. The first unit comprises a first structure configured to be associated with an aircraft structure for the aircraft. The first unit further comprises a first piezoelectric transducer associated with the first structure. The piezoelectric transducer has an elongate shape. The first unit further comprises a first array of piezoelectric transducers associated with the first structure. The first array of piezoelectric transducers is substantially parallel to the first transducer. The second unit comprises a second structure configured to be associated with the aircraft structure. The second unit further comprises a second piezoelectric transducer associated with the second structure. The second piezoelectric transducer has an elongate shape. The second unit further comprises a second array of piezoelectric transducers associated with the second structure. The second array of piezoelectric transducers is substantially parallel to the second piezoelectric transducer.

In yet another advantageous embodiment, a method for monitoring an object is provided. A first unit is associated with a first location in an object. The first unit comprises a first transducer having an elongate shape and a first array of transducers arranged substantially parallel to the first transducer. A second unit is associated with a second location in an object. The second unit comprises a second transducer having an elongate shape and a second array of transducers arranged substantially parallel to the second transducer. An inspection of the object is performed using the first unit and the second unit.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives, and advantages thereof, will best be understood by reference to the following detailed description of an advantageous embodiment of the present disclosure when read in conjunction with the accompanying drawings, wherein:

DETAILED DESCRIPTION

Figure 1:
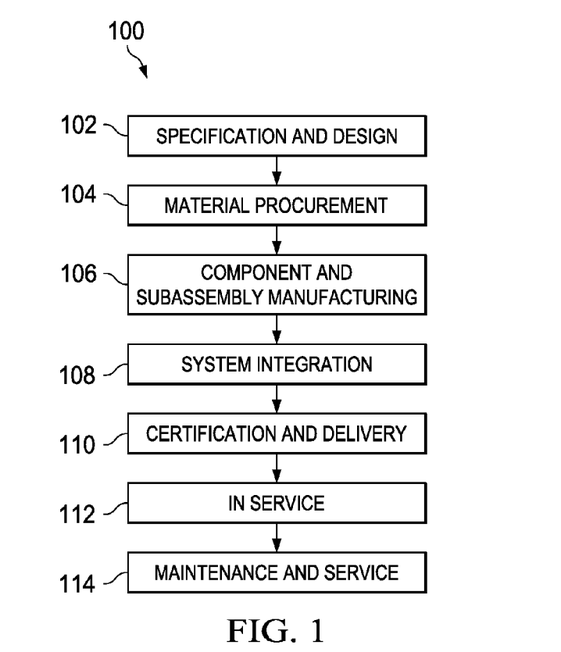
FIG. 1 is an illustration of an aircraft manufacturing and service method in accordance with an advantageous embodiment.
Figure 2:
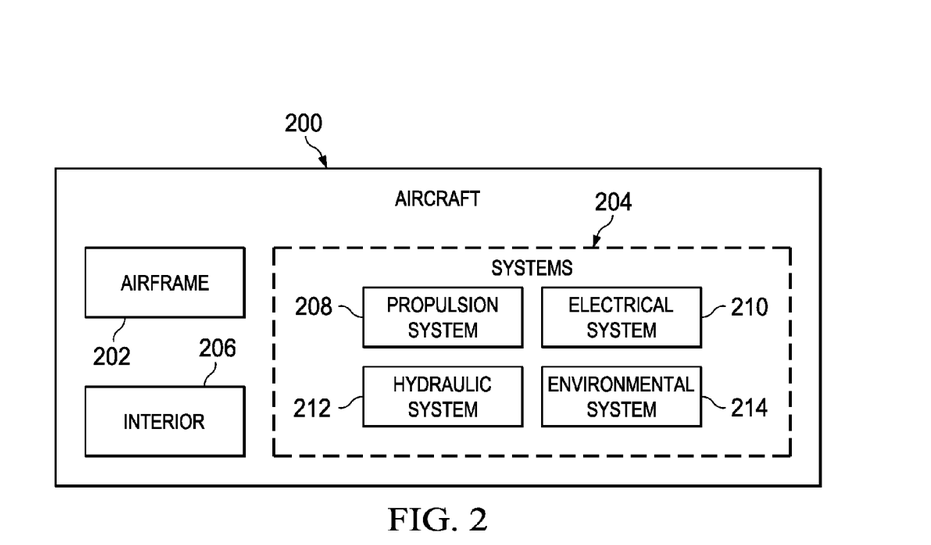
FIG. 2 is an illustration of an aircraft in which an advantageous embodiment may be implemented.

Referring more particularly to the drawings, embodiments of the disclosure may be described in the context of aircraft manufacturing and service method 100 as shown in FIG. 1 and aircraft 200 as shown in FIG. 2. Turning first to FIG. 1, an illustration of an aircraft manufacturing and service method is depicted in accordance with an advantageous embodiment. During pre-production, aircraft manufacturing and service method 100 may include specification and design 102 of aircraft 200 in FIG. 2 and material procurement 104.

During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service 112 by a customer, aircraft 200 in FIG. 2 is scheduled for routine maintenance and service 114, which may include modification, reconfiguration, refurbishment, and other maintenance or service.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 2, an illustration of an aircraft is depicted in which an advantageous embodiment may be implemented. In this example, aircraft 200 is produced by aircraft manufacturing and service method 100 in FIG. 1 and may include airframe 202 with plurality of systems 204 and interior 206. Examples of systems 204 include one or more of propulsion system 208, electrical system 210, hydraulic system 212, and environmental system 214. Any number of other systems may be included. Although an aerospace example is shown, different advantageous embodiments may be applied to other industries, such as the automotive industry.

Apparatuses and methods embodied herein may be employed during at least one of the stages of aircraft manufacturing and service method 100 in FIG. 1. As used herein, the phrase "at least one of", when used with a list of items, means that different combinations of one or more of the listed items may be used and only one of each item in the list may be needed. For example, "at least one of item A, item B, and item C" may include, for example, without limitation, item A, or item A and item B. This example also may include item A, item B, and item C, or item B and item C.

In one illustrative example, components or subassemblies produced in component and subassembly manufacturing 106 in FIG. 1 may be fabricated or manufactured in a manner similar to components or subassemblies produced while aircraft 200 is in service 112 in FIG. 1. As yet another example, a number of apparatus embodiments, method embodiments, or a combination thereof may be utilized during production stages, such as component and subassembly manufacturing 106 and system integration 108 in FIG. 1. A number, when referring to items, means one or more items. For example, a number of apparatus embodiments is one or more apparatus embodiments.

A number of apparatus embodiments, method embodiments, or a combination thereof may be utilized while aircraft 200 is in service 112 and/or during maintenance and service 114 in FIG. 1. More specifically, one or more of the different advantageous embodiments may be used to perform inspections during at least one of component and subassembly manufacturing 106, system integration 108, maintenance and service 114, and other suitable phases in aircraft manufacturing and service method 100. The use of a number of the different advantageous embodiments may substantially expedite the assembly of and/or reduce the cost of aircraft 200.

The different advantageous embodiments recognize and take into account a number of different considerations. For example, the different advantageous embodiments recognize and take into account that when inspections are performed by a human operator, the inspections of different locations are subject to interpretations of the data made by the human operator. As a result, a desired uniformity in results from inspections may not occur.

For example, a human operator may use an eddy current device to identify whether inconsistencies are located on a particular area. The human operator interprets the values to determine whether an undesired inconsistency is present. As a result, the inspections may be more subjective than desired.

Thus, one or more of the different advantageous embodiments provide a method and apparatus for performing non-destructive evaluation of objects. An apparatus comprises a structure, a transducer, and an array of transducers. The structure is configured to be associated with an object. This object may be an object for which non-destructive evaluation testing is desired. The transducer is associated with the structure. The transducer has an elongate shape. The array of transducers also is associated with the structure. The array of transducers is substantially parallel to the transducer. In other words, the array of transducers is arranged substantially parallel to the elongate shape of the transducer.

Figure 3:
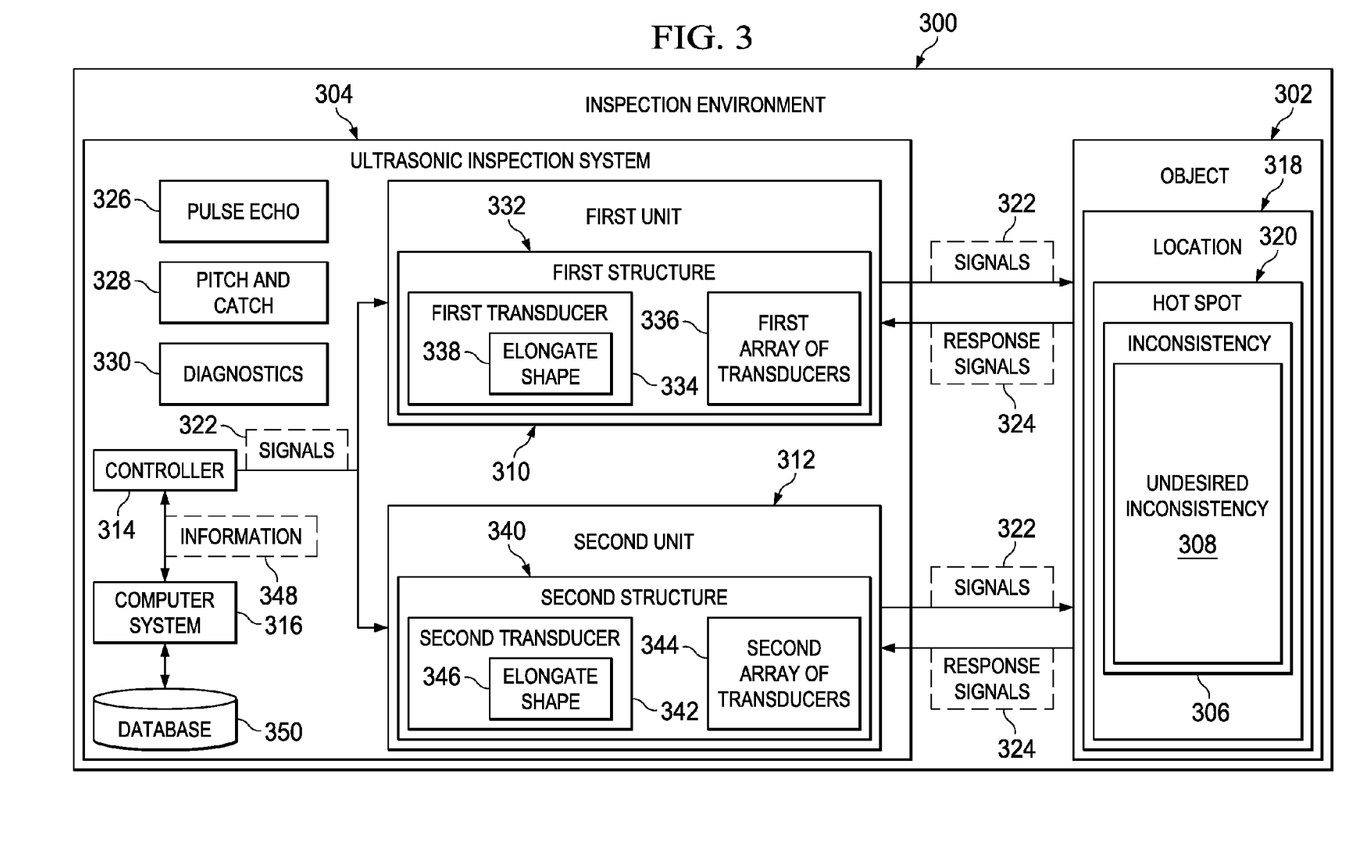
FIG. 3 is an illustration of an inspection environment in accordance with an advantageous embodiment.

With reference now to FIG. 3, an illustration of an inspection environment is depicted in accordance with an advantageous embodiment. In this illustrative example, inspection environment 300 is used to perform an inspection of object 302. Object 302 may be, for example, aircraft 200 in FIG. 2 and/or an aircraft structure on aircraft 200.

In this illustrative example, ultrasonic inspection system 304 is used to inspect object 302. In these illustrative examples, ultrasonic inspection system 304 may inspect object 302 during particular periods of time or may continuously monitor object 302, depending on the particular implementation. Ultrasonic inspection system 304 is used to test object 302 and determine whether inconsistency 306 is present in object 302.

Further, ultrasonic inspection system 304 may be used to determine whether inconsistency 306 is undesired inconsistency 308. In these illustrative examples, an undesired inconsistency may be an inconsistency that requires an action to be taken with respect to the inconsistency. The action may be, for example, reworking, replacement, or some other suitable action.

In this illustrative example, ultrasonic inspection system 304 comprises first unit 310, second unit 312, controller 314, and computer system 316. First unit 310 and second unit 312 are configured to be placed in location 318 in object 302.

In these illustrative examples, first unit 310 and second unit 312 may be placed on either side of hot spot 320 in location 318. Hot spot 320 is a location in which inconsistency 306 and undesired inconsistency 308 may be present or may occur. First unit 310 and second unit 312 are placed such that hot spot 320 is located between the two units.

First unit 310 comprises first structure 332, first transducer 334, and first array of transducers 336. First structure 332 is configured to be associated with object 302.

This association is a physical association in these examples. A first component, such as first structure 332, may be considered to be associated with a second component, such as object 302, by being secured to the second component, bonded to the second component, mounted to the second component, placed on the second component, welded to the second component, fastened to the second component, mechanically fastened to the second component, removably attached to the second component, and/or connected to the second component in some other suitable manner. The first component also may be connected to the second component using a third component. The first component may also be considered to be associated with the second component by being formed as part of and/or an extension of the second component.

In this manner, first structure 332 may be associated with object 302 in a number of different ways. First structure 332 may be, for example, a housing for first transducer 334 and/or first array of transducers 336. The housing may be attached to object 302 to perform testing of object 302. In some illustrative examples, first structure 332 may be a structure in object 302. For example, in some cases, when object 302 takes the form of an aircraft, first structure 332 may be a spar or rib in the aircraft.

In these illustrative examples, first transducer 334 is associated with object 302. In particular, first transducer 334 may be associated with object 302 by being associated with first structure 332. As depicted, first transducer 334 has elongate shape 338. Elongate shape 338 may be, for example, a rectangular shape.

A transducer is a device that converts one type of energy into another type of energy. In these illustrative examples, a transducer may generate signals 322. These signals are vibration signals. Signals 322 may be, for example, ultrasonic signals. These signals may have a frequency from about 0.1 megahertz (MHz) to about 50 megahertz.

In these illustrative examples, first array of transducers 336 in first unit 310 are also associated with object 302. First array of transducers 336 may be associated with object 302 by being associated with first structure 332. "An array of items", as used herein, means two or more items. In other words, "an array of transducers" means two or more transducers. In these illustrative examples, first array of transducers 336 may have a shape selected from at least one of a circle, a square, a pentagon, a hexagon, an octagon, and/or some other suitable shape.

First array of transducers 336 is substantially parallel to first transducer 334. In particular, first array of transducers 336 may be arranged substantially parallel to elongate shape 338 for first transducer 334.

Second unit 312 comprises second structure 340, second transducer 342, and second array of transducers 344. Second structure 340 is configured to be associated with object 302. Further, second transducer 342 is associated with object 302 and has elongate shape 346. Second transducer 342 may be associated with object 302 by being associated with second structure 340.

Similarly, second array of transducers 344 is associated with object 302. Second array of transducers 344 may be associated with object 302 by being associated with second structure 340. Second array of transducers 344 is substantially parallel to second transducer 342. In particular, second array of transducers 344 may be arranged in a manner that is substantially parallel to elongate shape 346 of second transducer 342. Further, second array of transducers 344 also may have a shape selected from at least one of a circle, a square, a pentagon, a hexagon, an octagon, and/or some other suitable shape.

In these illustrative examples, first transducer 334, transducers in first array of transducers 336, second transducer 342, and transducers in second array of transducers 344 may take the form of piezoelectric transducers (PZTs). Further, each of these piezoelectric transducers may be implemented as a transmitter, a sensor, or a transmitter and sensor. For example, first transducer 334 may be a first piezoelectric transducer, second transducer 342 may be a second piezoelectric transducer, first array of transducers 336 may be a first array of piezoelectric transducers, and second array of transducers 344 may be a second array of piezoelectric transducers.

In the form of a transmitter, the piezoelectric transducer is configured to transmit signals 322. In the form of a sensor, the piezoelectric transducer is configured to detect response signals 324 generated in response to the transmission of signals 322. When functioning to detect response signals 324, the piezoelectric transducer is also referred to as a receiver in addition to being called a sensor. Further, when functioning as a transmitter and a sensor, the piezoelectric transducer may be configured to both transmit signals 322 and detect response signals 324.

The sending of signals 322 into object 302 and the detection of response signals 324 generated in response to signals 322 may be used to perform different types of testing for object 302. For example, the testing may include at least one of pulse echo 326, pitch and catch 328, diagnostics 330, and/or other suitable types of testing.

Pulse echo 326 involves sending signals 322 into object 302 from first transducer 334 and detecting response signals 324 using first array of transducers 336. Response signals 324 are generated in response to signals 322 traveling towards hot spot 320 in object 302. Response signals 324 may be detected by first array of transducers 336 when an inconsistency, such as inconsistency 306 in object 302, is present at hot spot 320. Response signals 324 may also be referred to as an echo for signals 322.

The detection of response signals 324 may be performed by one or more of first array of transducers 336. With this type of testing, second unit 312 may not be needed. Pulse echo 326 may be performed in a similar manner using second transducer 342 and second array of transducers 344 in second unit 312.

With pitch and catch 328, signals 322 may be sent into object 302 from first transducer 334, and response signals 324 may be detected by second array of transducers 344. This detection may be performed using one or more of second array of transducers 344. Similarly, pitch and catch 328 may also be performed by sending signals 322 into object 302 from second transducer 342 and detecting response signals 324 using first array of transducers 336. Again, this detection may be performed using one or more of first array of transducers 336.

Diagnostics 330 may be self-diagnostic testing. Diagnostics 330 for first unit 310 may include first transducer 334 sending signals 322 in object 302 directly to first array of transducers 336. In a similar manner, second transducer 342 may send signals 322 directly to second array of transducers 344.

Of course, in these illustrative examples, any transducer selected from first transducer 334, first array of transducers 336, second transducer 342, and second array of transducers 344 may be configured to send signals 322. Further, any transducer selected from first transducer 334, first array of transducers 336, second transducer 342, and second array of transducers 344 may be configured to detect response signals 324 and/or signals 322. In this manner, any combination of transducers may be used to perform pulse echo 326, pitch and catch 328, and/or diagnostics 330.

In these illustrative examples, controller 314 is configured to control the generation of signals 322 and detection of response signals 324 by first unit 310 and second unit 312. Controller 314 may be implemented using any suitable controller for an ultrasonic inspection system. For example, Scan Sensory® and ScanGene® are examples of devices that may be used to implement controller 314. These devices are available from Acellent Technologies, Inc.

As depicted, controller 314 is configured to generate information 348 when response signals 324 are received by controller 314 and at least one of first unit 310 and second unit 312. Controller 314 may communicate with first unit 310 and second unit 312 through wired and/or wireless communications links.

Computer system 316 comprises one or more computers. When more than one computer is present in computer system 316, the computers may be in communication with each other. In these illustrative examples, computer system 316 receives information 348 generated by controller 314 in response to controller 314 receiving response signals 324.

Computer system 316 may communicate with controller 314 through wired or wireless communications links, depending on the particular implementation. In some illustrative examples, computer system 316 may be configured to send commands to controller 314 to control the operation of at least one of first transducer 334, first array of transducers 336, second transducer 342, and second array of transducers 344.

Information 348 may be stored in database 350. By storing information 348 in database 350, a history of information 348 may be created. This history may be used to determine when and how often testing may be performed. In some cases, if first unit 310 and second unit 312 are connected through object 302 or formed as part of object 302, the testing may occur on a more frequent basis that may be referred to as monitoring.

With ultrasonic inspection system 304, the detection of inconsistencies, such as inconsistency 306, may be performed in a more desirable fashion. With the use of first unit 310 and second unit 312, the number of inspections performed by human operators moving around object 302 may be reduced. For example, first unit 310 and second unit 312 may be permanently placed on or removably attached to object 302 in these depicted examples.

The placement of first unit 310 and second unit 312 may be selected to monitor areas of interest, such as hot spot 320. With the placement of these units on object 302, hot spot 320 may be routinely inspected or monitored on a consistent basis. These inspections may be performed without requiring human operators to go to location 318 each time. As a result, when areas that are difficult to access by human operators are present, the inspection of these areas may be more easily performed through the use of ultrasonic inspection system 304.

The illustration of inspection environment 300 in FIG. 3 is not meant to imply physical or architectural limitations to a manner in which an advantageous embodiment may be implemented. Other components in addition to and/or in place of the ones illustrated may be used. Some components may be unnecessary. Also, the blocks are presented to illustrate some functional components. One or more of these blocks may be combined and/or divided into different blocks when implemented in an advantageous embodiment.

For example, in some illustrative examples, one or more units in addition to first unit 310 and second unit 312 may be used in location 318 around hot spot 320. For example, additional units may be placed in different locations around hot spot 320.

In other illustrative examples, computer system 316 may not be considered as part of ultrasonic inspection system 304. In still other illustrative examples, controller 314 may be part of computer system 316.

In some illustrative examples, additional components may be present in first unit 310 and/or second unit 312. For example, communications units may be included in first unit 310 and second unit 312. These communications units may be, for example, wireless network interface cards, transceivers, and/or other suitable types of communications units.

Further, as another example, blocks for power not shown in these illustrative examples may be present in ultrasonic inspection system 304 in other illustrative examples. Further, the powering of the different components in ultrasonic inspection system 304 may occur through wired connections, wireless power transmission, or a combination of the two.

In still other illustrative examples, object 302 may not be an aircraft or a structure for an aircraft. For example, object 302 may be some other type of vehicle, a structure for some other type of vehicle, or some other suitable type of object. More specifically, object 302 may be selected from one of a mobile platform, a stationary platform, a land-based structure, an aquatic-based structure, a space-based structure, a surface ship, a tank, a personnel carrier, a train, a spacecraft, a space station, a satellite, a submarine, an automobile, a power plant, a bridge, a dam, a manufacturing facility, a building, an engine housing, a skin panel, a wing, a rib, a spar, and/or some other suitable type of object.

Figure 4:
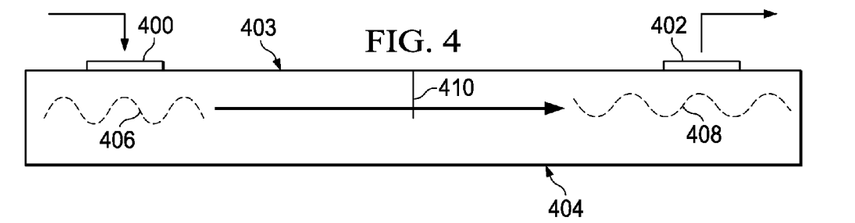
FIG. 4 is an illustration of transducers being used to perform pitch and catch testing of an object in accordance with an advantageous embodiment.

With reference now to FIG. 4, an illustration of transducers being used to perform pitch and catch testing of an object is depicted in accordance with an advantageous embodiment. In this illustrative example, transducer 400 and transducer 402 are associated with surface 403 of object 404. In particular, these transducers are attached to surface 403 of object 404.

Transducer 400 and transducer 402 are used to perform pitch and catch testing of object 404 in this illustrative example. Transducer 400 is an example of one implementation for first transducer 334 or second transducer 342 in FIG. 3. Transducer 402 is an example of one implementation for one of first array of transducers 336 or one of second array of transducers 344.

In these depicted examples, transducer 402 is a piezoelectric transducer in the form of a transmitter. Transducer 400 is a piezoelectric transducer in the form of a receiver. Transducer 400 is configured to send signal 406 into object 404. Transducer 402 is configured to detect response signal 408 generated in response to signal 406 being sent in object 404.

As depicted, response signal 408 is generated in response to signal 406 traveling past inconsistency 410 in object 404. Response signal 408 may also be referred to as a forward scattered waveform in this illustrative example.

Figure 5:
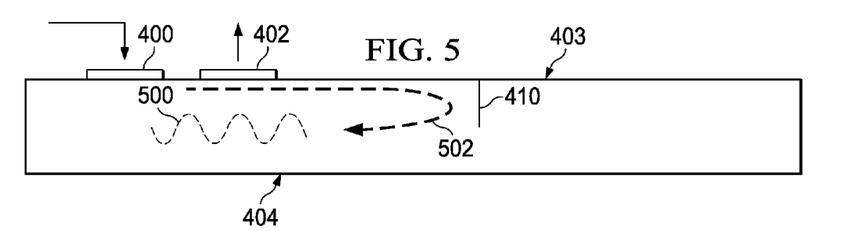
FIG. 5 is an illustration of transducers being used to perform pulse echo testing of an object in accordance with an advantageous embodiment.

Turning now to FIG. 5, an illustration of transducers being used to perform pulse echo testing of an object is depicted in accordance with an advantageous embodiment. In this illustrative example, transducer 400 and transducer 402 from FIG. 4 are used to perform pulse echo testing of object 404.

As illustrated, transducer 400 is configured to send signal 500 into object 404. Transducer 402 is configured to detect response signal 502 generated in response to signal 500 being sent in object 404. In particular, response signal 502 is detected in response to signal 500 encountering inconsistency 410 in object 404 and being reflected back. Response signal 502 may also be referred to as an echo, a back scattered waveform, or a reflected waveform.

Figure 6:
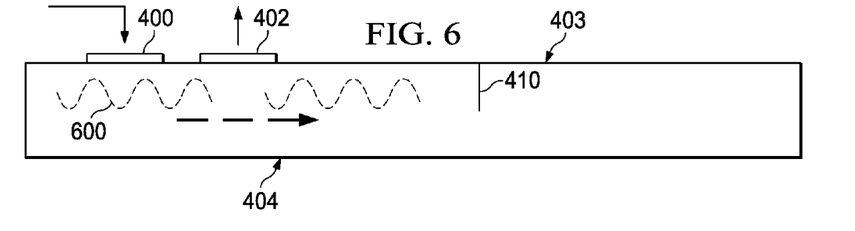
FIG. 6 is an illustration of transducers being used to perform diagnostic testing in accordance with an advantageous embodiment.

With reference now to FIG. 6, an illustration of transducers being used to perform diagnostic testing is depicted in accordance with an advantageous embodiment. In this illustrative example, transducer 400 and transducer 402 from FIG. 4 are used for self-diagnostics. In particular, transducer 400 is configured to send signal 600 directly to transducer 402 such that signal 600 does not encounter inconsistency 410 in object 404. Transducer 402 is configured to detect signal 600.

Figure 7:
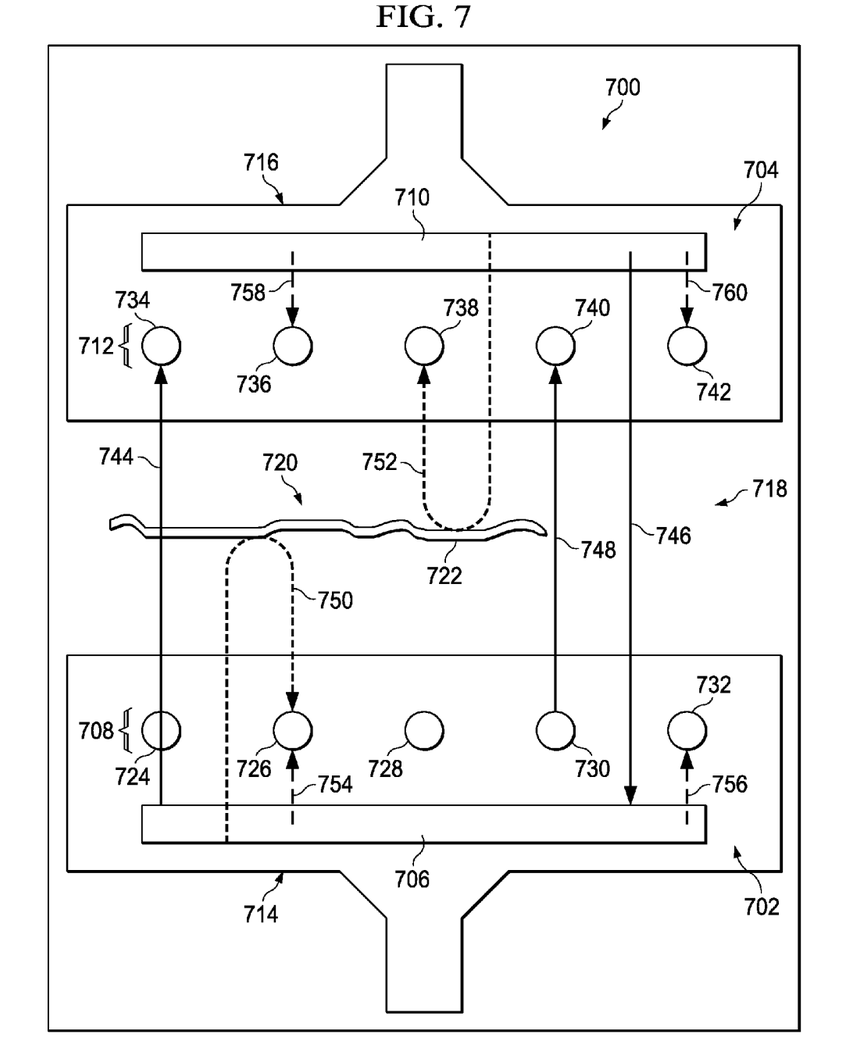
FIG. 7 is an illustration of an ultrasonic inspection system for testing a hot spot in accordance with an advantageous embodiment.

With reference now to FIG. 7, an illustration of an ultrasonic inspection system for testing a hot spot is depicted in accordance with an advantageous embodiment. In this illustrative example, ultrasonic inspection system 700 is an example of one implementation for ultrasonic inspection system 304 in FIG. 3.

As depicted, ultrasonic inspection system 700 comprises first unit 702 and second unit 704. First unit 702 includes first transducer 706 and first array of transducers 708. Second unit 704 includes second transducer 710 and second array of transducers 712.

First transducer 706 and first array of transducers 708 in first unit 702 are associated with first structure 714. Second transducer 710 and second array of transducers 712 are associated with second structure 716. First structure 714 and second structure 716 may be associated with object 718.

First unit 702 and second unit 704 are positioned around hot spot 720 in object 718. Hot spot 720 is a location at which inconsistency 722 is present in these examples. In other illustrative examples, hot spot 720 may be a location at which an inconsistency may be expected to occur over time.

As one illustrative example, ultrasonic inspection system 700 may be used to test inconsistency 722 to determine whether inconsistency 722 is an undesired inconsistency that requires maintenance. For example, first unit 702 and second unit 704 may be used to test object 718 at hot spot 720 to determine whether inconsistency 722 is greater than a selected threshold.

As depicted, first array of transducers 708 includes transducers 724, 726, 728, 730, and 732. Second array of transducers 712 includes transducers 734, 736, 738, 740, and 742. In this illustrative example, pitch and catch test 744 is performed using first transducer 706 and transducer 734, with first transducer 706 sending the signals and transducer 734 detecting the response signals.

Pitch and catch test 746 is performed using second transducer 710 and first transducer 706, with second transducer 710 sending the signals and first transducer 706 detecting the response signals. Pitch and catch test 748 is performed using transducer 730 to send signals and transducer 740 to detect the response signals.

Further, pulse echo test 750 is performed using first transducer 706 to send signals and transducer 726 to detect the response signals. Pulse echo test 752 is also performed using second transducer 710 to send signals and transducer 738 to detect the response signals.

As depicted, diagnostic test 754 is performed with first transducer 706 sending signals directly to transducer 726. Diagnostic test 756 is performed with first transducer 706 sending signals directly to transducer 732. Additionally, diagnostic test 758 is performed with second transducer 710 sending signals directly to transducer 736. Diagnostic test 760 is performed with second transducer 710 sending signals directly to transducer 742.

The different components shown in FIGS. 4-7 may be combined with components in FIG. 3, used with components in FIG. 3, or a combination of the two. Additionally, some of the components in these figures may be illustrative examples of how components shown in block form in FIG. 3 can be implemented as physical structures.

Figure 8:
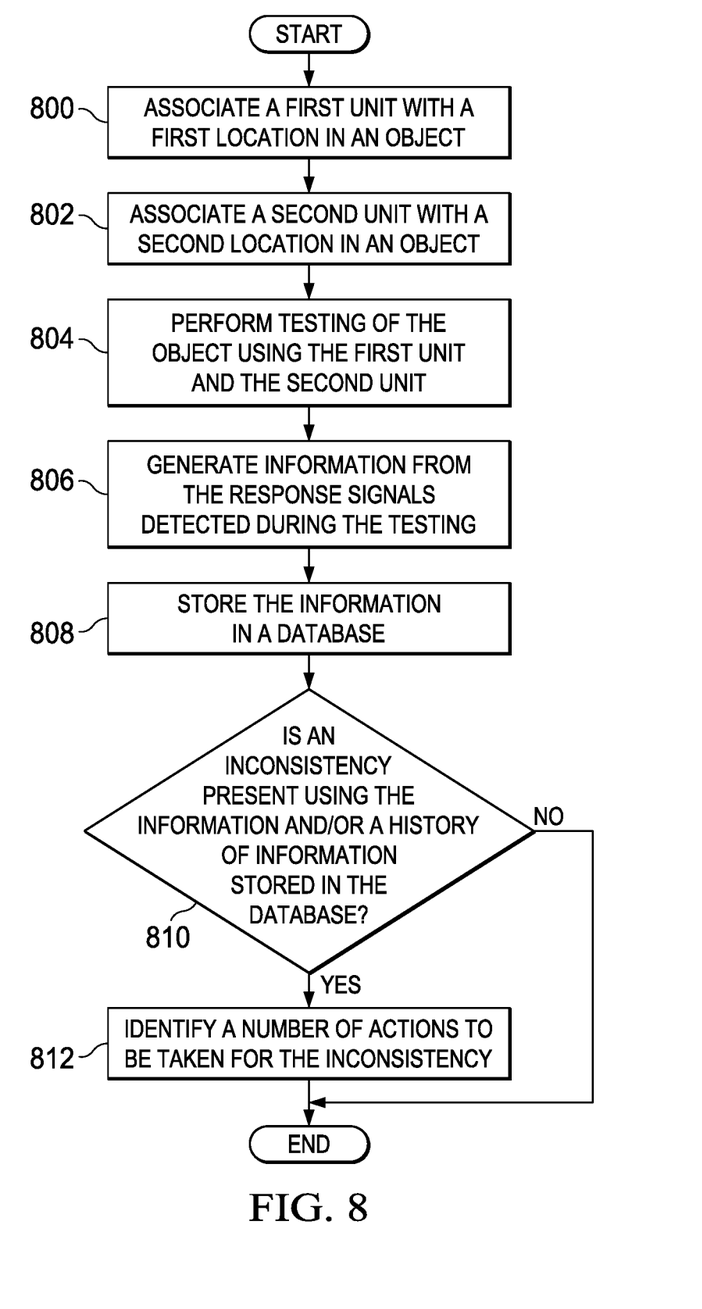
FIG. 8 is an illustration of a flowchart of a process for performing non-destructive evaluation testing in accordance with an advantageous embodiment.

With reference now to FIG. 8, an illustration of a flowchart of a process for performing non-destructive evaluation testing is depicted in accordance with an advantageous embodiment. The process illustrated in FIG. 8 may be implemented using ultrasonic inspection system 304 in FIG. 3.

The process begins by associating a first unit with a first location in an object (operation 800). In operation 800, the first unit comprises a first transducer having an elongate shape and a first array of transducers arranged substantially parallel to the elongate shape of the first transducer.

The process then associates a second unit with a second location in an object (operation 802). The second unit comprises a second transducer having the elongate shape and a second array of transducers arranged substantially parallel to the elongate shape of the second transducer.

The first location and the second location in the object may be locations around a hot spot in which an inconsistency is present or may occur. The first location and the second location may be substantially opposite to each other and on two sides of the hot spot.

In this illustrative example, operation 800 and operation 802 may be performed by placing the units on the object, attaching a housing for the units to the object, forming the units as part of the object, and/or associating the units with the object in some other manner. Of course, these units may be associated with the object in any of a number of different ways.

Thereafter, the process performs testing of the object using the first unit and the second unit (operation 804). This testing may be performed using pitch and catch testing and/or pulse echo testing.

Operation 804 includes sending signals from at least one of a first transducer, a transducer in the first array of transducers, the second transducer, and a transducer in the second array of transducers into the object. Further, operation 804 includes detecting response signals generated in response to the signals sent into the object by at least one of the first transducer, a transducer in the first array of transducers, the second transducer, and a transducer in the second array of transducers.

The process then generates information from the response signals detected during the testing (operation 806). Operation 806 may be performed using a controller configured to receive the response signals from the first unit and/or the second unit while and/or after the testing is performed. The process then stores the information in a database (operation 808).

Next, the process determines whether an inconsistency is present using the information and/or a history of information stored in the database (operation 810). If an inconsistency is present, the process identifies a number of actions to be taken for the inconsistency (operation 812), with the process terminating thereafter. Otherwise, if an inconsistency is not present, the process terminates.

In operation 812, the number of actions may include, for example, at least one of determining whether the inconsistency requires maintenance, creating a schedule for performing future inspections at the hot spot, reworking the inconsistency, performing additional testing at the hot spot, and/or other suitable actions.

The flowchart and block diagrams in the different depicted embodiments illustrate the architecture, functionality, and operation of some possible implementations of apparatuses and methods in an advantageous embodiment. In this regard, each block in the flowchart or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowchart or block diagrams.

In some alternative implementations of an advantageous embodiment, the function or functions noted in the block may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

For example, in some illustrative examples, operations 808, 810, and 812 may be omitted. In still other examples, operations 800 and 802 may not be performed each time testing occurs. The units may be associated with the object and left in place for future testing. In still other illustrative examples, the information for the response signals may be stored in the database only if the response signals are over a selected threshold.

Thus, the different advantageous embodiments provide a method and apparatus for performing non-destructive evaluation of objects. An apparatus comprises a transducer and an array of transducers. The transducer is associated with an object. This object may be an object for which non-destructive evaluation testing is desired. The transducer has an elongate shape. The array of transducers also is associated with the object. The array of transducers is arranged substantially parallel to the elongate shape of the transducer.

Non-destructive evaluation testing may be performed using the transducer and the array of transducers. This system allows testing to be performed without requiring disassembly and reassembly of structures in the object. In this manner, a number of inconsistencies in the data recorded during the inspection may be reduced.

The description of the different advantageous embodiments has been presented for purposes of illustration and description and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
    a single transducer associated with an object, wherein the transducer has an elongate shape;
    an array of transducers associated with the object, wherein the single transducer and the array of transducers are associated with the object by being one or more of: bonded to the object, placed on the object, formed as part of the object, or mechanically fastened to the object, wherein the array of transducers is substantially parallel to the single transducer, wherein the single transducer is configured to transmit a signal and the array of transducers is configured to detect a response signal to the signal transmitted by the transducer, and wherein the signal travels towards the object and is reflected from the object to generate the response signal;
    a controller configured to generate information using the response signal; and
    a computer system configured to perform an inspection of the object and to use the information to provide results based on the inspection.

2. The apparatus of claim 1, wherein the single transducer and the array of transducers are configured to send and receive signals for a diagnostic test of at least one of the single transducer and a number of transducers in the array of transducers.

3. The apparatus of claim 1, wherein the single transducer is a first single transducer; the array of transducers is a first array of transducers; and the first single transducer and the first array of transducers form a first unit and further comprising:
    a second unit comprising a second single transducer associated with the object, wherein the second single transducer has the elongate shape; and a second array of transducers associated with the object, wherein the second array of transducers is substantially parallel to the second single transducer.

4. The apparatus of claim 3, wherein the first unit and the second unit are configured such that when the first unit and the second unit are associated with the object, the first unit transmits the signal and the second unit receives the response signal; and the apparatus is further configured to perform the inspection using the first unit to transmit the signal and the second unit to receive the response signal.

5. The apparatus of claim 1, wherein the single transducer and the array of transducers are associated with the object by being associated with a structure configured to be associated with the object by being bonded to the object, placed on the object, formed as part of the object, or mechanically fastened to the object.

6. The apparatus of claim 1 further comprising:
    the controller being connected to the single transducer and the array of transducers, wherein the controller is configured to control operation of the single transducer and the array of transducers.

7. The apparatus of claim 6, wherein:
    the computer system is configured to send commands to the controller to control the operation of the single transducer and the array of transducers and receive the information generated by the controller in response to the controller receiving the response signal.

8. The apparatus of claim 1, wherein the single transducer is selected from one of a sensor, a transmitter, or a combination of the sensor and the transmitter.

9. The apparatus of claim 1, wherein the elongate shape for the single transducer is a rectangular shape.

10. The apparatus of claim 1, wherein transducers in the array of transducers have a shape selected from at least one of a circle, a square, a pentagon, a hexagon, or an octagon.

11. The apparatus of claim 1, wherein the single transducer and transducers in the array of transducers are piezoelectric transducers.

12. The apparatus of claim 1, wherein the array of transducers are positioned such that the array of transducers extends along a length of the single transducer.

13. A nondestructive evaluation system for an aircraft, the nondestructive evaluation system comprising:
a first unit comprising:
a first housing configured to be associated with an aircraft structure of the aircraft, wherein a first piezoelectric transducer is housed within the first housing, wherein the first piezoelectric transducer has an elongate shape and comprises a single transducer, wherein a first array of piezoelectric transducers is housed within the first housing, and wherein the first array of piezoelectric transducers is substantially parallel to the first piezoelectric transducer;
a second unit comprising:
a second housing configured to be associated with the aircraft structure, wherein a second piezoelectric transducer is housed within the second housing, wherein the second piezoelectric transducer has the elongate shape and comprises a single transducer, wherein a second array of piezoelectric transducers is housed within the second housing, and wherein the second array of piezoelectric transducers is substantially parallel to the second piezoelectric transducer;
wherein the first housing and the second housing are configured to be associated with the aircraft structure by being one or more of: bonded to the aircraft structure, placed on the aircraft structure, formed as part of the aircraft structure, or mechanically fastened to the aircraft structure, and
wherein the first unit and the second unit are configured such that when the first unit and the second unit are associated with the aircraft structure, the first unit transmits a signal that travels towards the aircraft structure, and the second unit receives a response signal, wherein the signal is reflected from the aircraft structure or transmitted through the aircraft structure to generate the response signal;
a controller configured to generate information using the response signal; and
a computer system configured to perform an inspection of the aircraft structure and to use the information to provide results based on the inspection.

14. A method for monitoring an object, the method comprising:
associating a first unit with a first location in an object, wherein the first unit comprises a first single transducer having an elongate shape and a first array of transducers arranged substantially parallel to the first single transducer;
associating a second unit with a second location in the object, wherein the second unit comprises a second single transducer having the elongate shape and a second array of transducers arranged substantially parallel to the second single transducer,
wherein the first unit and the second unit are respectively associated with the first and second locations in the object by being one or more of: bonded to the object, placed on the object, formed as part of the object, or mechanically fastened to the object;
using the first unit to transmit a signal and the second unit to receive a response signal,
wherein the signal travels toward the object and is reflected back from the object or is transmitted through the object to generate the response signal;
generating information using the response signal;
performing an inspection of the object using the information; and
providing results based on the inspection.

15. The method of claim 14, wherein the first location is on a first side of a hot spot, the second location is on a second side of the hot spot, and the first side is substantially opposite to the second side.

16. The method of claim 14, wherein performing the inspection of the object using the first unit and the second unit comprises:
performing the inspection of the object using the first unit and the second unit and at least one of a pulse echo test and a pitch and catch test.

17. An apparatus comprising:
a transducer associated with an object, wherein the transducer has a continuously elongate shape;
an array of transducers associated with the object, wherein the transducer and the array of transducers are associated with the object by being one or more of: bonded to the object, placed on the object, formed as part of the object, or mechanically fastened to the object, wherein the array of transducers is substantially parallel to the transducer, wherein the transducer is configured to transmit a signal and the array of transducers is configured to detect a response signal to the signal transmitted by the transducer, and wherein the signal travels towards the object and is reflected from the object to generate the response signal;
a controller configured to generate information using the response signal; and
a computer system configured to perform an inspection of the object and to use the information to provide results based on the inspection.

* * * * *